United States Patent [19]
Nesburn et al.

[11] Patent Number: 5,679,348
[45] Date of Patent: Oct. 21, 1997

[54] IMMUNOTHERAPY FOR RECURRENT HSV INFECTIONS

[75] Inventors: Anthony Bart Nesburn, Malibu; Steven Lewis Wechsler, Westlake Village; Homayon Ghiasi, Los Angeles, all of Calif.

[73] Assignee: Cedars-Sinai Medical Center, Los Angleles, Calif.

[21] Appl. No.: 829,947

[22] Filed: Feb. 3, 1992

[51] Int. Cl.$^6$ .................... A61K 39/12; A61K 39/245; C07K 14/035; C12N 7/00
[52] U.S. Cl. .................... 424/186.1; 424/229.1; 435/235.1; 514/12; 530/826
[58] Field of Search ................. 435/320.1, 69.1, 435/69.3, 240.2, 172.3, 235, 235.1; 424/89, 186.1, 229.1; 514/8, 12; 530/395, 826

[56] References Cited

U.S. PATENT DOCUMENTS

| | | | |
|---|---|---|---|
| 4,891,315 | 1/1990 | Watson et al. | 435/69.3 |
| 5,171,568 | 12/1992 | Burke et al. | 424/186.1 |
| 5,244,792 | 9/1993 | Burke et al. | 435/69.3 |

FOREIGN PATENT DOCUMENTS

| | | |
|---|---|---|
| 0243155 | 10/1987 | European Pat. Off. . |
| 0297924 | 1/1989 | European Pat. Off. . |
| 85/04587 | 10/1985 | WIPO . |

OTHER PUBLICATIONS

Ghiasi H. et at., High level expression of each of the seven herpes simplex virus glycoproteins in insect cells using baculovirus expression vectors: subsequent use as vaccines, Invest. Ophthalmol. Visual Sci., vol. 32, No. 4, p. 806 (1991) Abstract 686.

Kino Y. et at., Immunogenicity of herpes simplex virus glycoprotein gB–1–related protein produced in yeast, Vaccine, 7:155–160 (1989).

Nesburn A. et al., Efficacy and safety of therapeutic systemic HSV vaccines in the rabbit ocular recurrence model, Invest. Ophthalmol. Visual Sci., vol. 32, No. 4, p. 854 (1991) Abstract 917.

Klein, R.J., Reinfections and site–specific immunity in herpes simplex virus infections. Vaccine, 7:380–381 (1989).

Stanberry, L.R. et al., Herpes simplex virus glycoprotein treatment of recurrent genital herpes. J. Infec. Dis., 157:156–63 (1988).

Kern, A.B. et al., Vaccine Therapy in Recurrent Herpes Simplex. Arch. Derm., 89:844–845 (1964).

Frenkel, L. et al., A randomized double blind, placebo–controlled phase 1 trial of a herpes simplex virus purified glycoprotein (gD1) vaccine. Interscience Conf. on Antimicrobial Agents & Chemo., 206 (1990).

Berman, P.W. et al., Efficacy of Recombinant Glycoprotein D Subunit Vaccines on the Development of Primary, Recurrent, and Latent Genital Infections With Herpes Simplex Virus Type 2 in Guinea Pigs. J. Infec. Dis., 157(5):897–902 (May 1988).

Blacklaws, B. et al., Immunogenicity of herpes simplex type 1 glycoproteins expressed in vaccinia virus recombinants. Virology, 177:727–736 (1990).

Stanberry, L.R. et al., Heterologous Versus Homologous Herpes Simplex Virus Glycoprotein Immunotherapy of Recurrent Genital Herpes. Pediatr. Res., 25:191A, Part 2 (1989).

Rock, D.L., Nesburn, A.B. et al., Detection of latency related viral RNAs in trigeminal ganglia of rabbits latently infected with herpes simplex virus type 1. J. Virol., 61:3820–26 (1987).

Matsuura, Y. et al., Baculovirus expression vectors: the requirements for high level expression of proteins, including glycoproteins. J. Gen. Virol., 68:1233–50 (1987).

Lee, G.T. et al., Location of the structural genes for glycoproteins gD and gE and for other polypeptides in the S component of herpes simplex virus type 1 DNA. J. Virol., 43:41–49 (1982).

Mathews, J.T. et al., Synthesis and processing glycoprotein D of herpes simplex virus types 1 and 2 in an in vitro system. J. Virol., 48:521–53 (1983).

Ghiasi, H., et al., Cell surface expression of herpes simplex virus type 1 glycoprotein H recombinant baculovirus infected cells. Virology, 185:187–194 (1991).

Morein, B. et al., Iscom, a novel structure for antigenic presentation of membrane proteins from enveloped viruses. Nature, 308:457–60 (1984).

Shimormura, Y. et al., Shedding by iontophoresis of 6–hydroxdopamine followed by topical epinephrine. Invest. Ophthalmol., 24:1588–90 (1983).

Nesburn, A.B. et al., Isolation of herpes simplex virus: Isolation from rabbit trigeminal ganglia between episodes of recurrent ocular infection. Arch. Ophthalmol., 88:412–17 (1972).

Nesburn, A.B. et al., Ocular safety and efficacy of an HSV–1 gD vaccine during primary and latent infection. Invest. Ophthalmol. Vis. Sci., 31:77–82 (1990).

Krishna et al (1989) J. gen. Virol. 70 1805–1814.
George et al. (1988) Am. J. Vet. Res. 49 1800–1806.
Miskin et al. Vaccine 9:147–153 (1991).
Kino et al. Arch. Virol. 89:69–80 (1986).
Lucknow et al. (1988) Biotechnology 6:47–55.
Gompels et al (1986) Virology 153:230–247.
Ghiasi, H. et al. Virus Research 22:25–39 (1991).

Primary Examiner—Robert A. Wax
Assistant Examiner—Dian C. Jacobson
Attorney, Agent, or Firm—Lyon & Lyon

[57] ABSTRACT

Immunotherapy for the treatment of Herpes Simplex Virus eye infections is disclosed. The invention involves a local therapeutic or prophylactic vaccine for the eye, comprising one or more recombinant HSV-1 glycoproteins or proteins, specifically gB and gD, in combination with at least one adjuvant to reduce the incidence of primary HSV-1 infection and/or decrease spontaneous HSV-1 ocular shedding which in turn, controls recurrent corneal disease.

6 Claims, 5 Drawing Sheets

IMMUNOTHERAPY FOR RECURRENT HSV INFECTIONS

I. FIELD OF THE INVENTION

The present invention relates to the field of infectious diseases and ophthalmology.

II. BACKGROUND OF THE INVENTION

A. Incidence and Course of HSV Infection

Herpes Simplex Virus (HSV), also known as *herpesvirus hominis*, is classified into two (2) types, 1 and 2. HSV-1 is transmitted by physical contact, such as kissing, and is thus spread among family members and friends. About half of all babies in the United States are born with IgG antibodies to this agent which is transmitted across the placenta. As this immunity dissipates, new infections are acquired until, by age 45, close to 70% of people have become serologically positive—most without ever experiencing signs of disease, others after one or several episodes of fever blisters or cold sores.

In contrast, HSV-2, also called genital herpes, is transmitted during birth or by sexual contact. The latter's incidence rises with the number of sexual partners and has therefore greatly increased in today's society. Compared with HSV-1, genital herpes is less prevalent overall but is likewise cumulative with age. In addition, genital herpes has engendered considerable anxiety because there is tenuous evidence that it may contribute to the causation of cervical cancer, and because of the risk of vertical transmission during childbirth inducing serious disease. Infections with both causative agents are difficult to prevent; and there is as yet no proven vaccine for the prophylaxis of genital herpes. Moreover, an ocular vaccine for the prophylaxis of ocular HSV has not been tried in humans.

Turning specifically to HSV-1, it is the most common infectious cause of blindness in industrial nations (1). The often prolonged ocular disease results in considerable visual morbidity, medical expense and loss of productivity in otherwise healthy individuals. Approximately 500,000 cases of ocular HSV-1 are diagnosed annually in the United States alone; and 25% to 45% of these cases may be expected to recur within 1 to 2 years after the primary disease episode (1). Of note, the majority of cases diagnosed as primary HSV are actually recurrent infections, as the patient may not recall the antecedent attack. Recurrence is therefore the hallmark of HSV infection.

After primary HSV infection occurs, the virus can travel in the nerves to the neurons in the trigeminal ganglia, where it then persists throughout life. This critical factor presently makes the herpes simplex infection an incurable disease, since the virus eventually may travel back down these nerves and reinfect the part of the body innervated by that nerve. Various trigger mechanisms such as trauma, fever, sunlight exposure or stress may initiate the reactivation process. This latency-reactivation-recurrence cycle results in ocular virus shedding despite a good local ocular IgA response to the virus (2). Once HSV has recurred in the eye, corneal disease and stromal scarring can follow, resulting in corneal blindness. Over 1,000 corneal transplants per year are currently performed in the U.S. as a direct result of HSV scarring. Hence, on recovering from the initial HSV infection, the stage is set for reinfection from one's own herpes virus for the remainder of the individual's life.

Since recurrences continue throughout the lifetime of the infected individual, it is clear that natural HSV infection affords insufficient protection against HSV recurrences. Moreover, individuals infected with one HSV serotype are only partially protected against subsequent infection with the other serotype; while individuals with non-ocular HSV-1 are not protected against subsequent ocular HSV-1 infection. Virus from a recurrent lesion on the body can be transferred to the eye, which is thought by some to be a common mode of contracting ocular infections. Because repeated recurrences of HSV do not elicit an immune response that prevents additional recurrences, there is a critical need to elicit a stronger, or perhaps a different immune response than that elicited by natural HSV-1 infection.

With further regard to immune protection, it appears that both antibody and cell-mediated immunity (CMI) are important in the control of HSV infection (3, 4, 5), although CMI may play a larger role. Patients with defects in CMI generally have more severe infection than those with impaired humoral immunity (6–10); whereas patients with frequently recurring HSV have high titers of anti-HSV antibodies. Ophthalmologists have also demonstrated that patients with exuberant immune responses, such as atopes, develop the worst clinical manifestations of stromal herpetic keratitis. Whereas immunosuppressed patients, in contrast, show exacerbated epithelial keratitis but minimal stromal disease. Hence, immunotherapy capable of inducing a specific higher than normal cellular immune response is needed to combat recurrent ocular HSV infections.

Another factor attributing to recurrent ocular HSV infection is the absence of blood vessels in the cornea. Because the cornea is devoid of blood vessels, systemic immune responses can be inefficient at providing protection from antigenic insults there (11). Consequently, local immunity may be particularly important in protection against ocular HSV. There is therefore the need for local ocular immunotherapy to augment the immune response and control recurrent ocular HSV infection.

Currently, commercial HSV vaccine development is directed exclusively to the problem of genital HSV-2. There is minimal effort directed to combat ocular HSV-1. Yet the development of a therapeutic vaccine, that is, a vaccine to reduce HSV ocular recurrences, would greatly alleviate what is now the most frequent serious viral eye infection in the U.S. and a major cause of viral induced blindness in the world. The present invention satisfies this need and provides related advantages as well. The disclosures of all publications cited herein are expressly incorporated by reference.

B. DNA Technology

Recombinant DNA and associated technologies can be applied to effectively provide the large quantities of high quality bioactive HSV glycoproteins and proteins required for a therapeutic or prophylactic HSV vaccine.

DNA technology involves in part, producing a replicable expression vehicle by the DNA recombination of an origin of replication, one or more phenotypic selection characteristics, an expression promoter, a heterologous gene insert and remainder vector. The resulting expression vehicle is introduced into cells by transformation and large quantities of the recombinant vehicle obtained by growing the transformant. Where the gene is properly inserted with reference to portions which govern the transcription and translation of the encoded DNA message, the expression vehicle may produce the polypeptide sequence for which the inserted gene codes. This process of producing the polypeptide is called "expression." The resulting product may be obtained by lysing the host cell, and recovering the product by appropriate purification.

A wide range of host cells can be used, including prokaryotic and eukaryotic organisms. In addition to microorganisms, cultures of cells derived from multicellular organisms, whether vertebrate or invertebrate, may also be used as hosts.

C. Definitions

As used in this disclosure, the following terms are to be understood in relation to the following definitions.

ADJUVANT: a substance that enhances, nonspecifically, the immune response to an antigen. An adjuvant is usually administered with antigen, but may also be given before or after antigen. Adjuvants disclosed within the subject invention include but are not limited to, alum, Freund's, MTP-PE, ISCOMs, Quil A and liposomes.

ALUM: antigen absorbed into floccules of aluminum salts. Alum is the only adjuvant currently approved by the FDA for human use.

EXPRESSION VECTOR: a vehicle used to carry inserted foreign (heterologous) DNA for the purpose of producing more material or a glycoprotein or protein product. "Expression vector" includes vectors which are capable of expressing the DNA sequences it contains, where such sequences are operably linked to other sequences capable of effecting their expression. Any DNA sequence which is capable of effecting expression of a specified DNA code disposed within the sequence is included in this term as it is applied to the specified sequence. In general, expression vectors of utility in recombinant DNA techniques are often in the form of plasmids; however, this invention is intended to include other forms of expression vectors which serve equivalent functions and which subsequently become known in the art.

FREUND'S: A water-in-oil emulsion. There are two forms of Freund's adjuvant, depending on the presence or absence of killed Mycobacteria. Complete Freund's adjuvant contains *Mycobacterium tuberculosis*, or other Mycobacteria strains. Weak antigens may be rendered more immunogenic when incorporated in complete Freund's adjuvant. Incomplete Freund's adjuvant lacks Mycobacteria and is less stimulatory.

GLYCOPROTEIN: a class of compounds in which protein is combined with carbohydrate.

MTP-PE: a new proprietary adjuvant developed by CIBA and refined by Chiron comprising M-acetylmuramyl-L-alanyl-B-isoglutaminyl-L-alanine-2-(1'-2'-dipalmitoyl-sn-glycerol-3-hydroxyphosphoryloxy)-ethylamine. It is a potent and well tolerated derivative of Freund's, and has proven to be much more effective than alum.

ISCOH (Quil A): immunostimulating complexes comprising purified proteins and the glycoside Quil A to form a honeycomb like structure that exhibits strong adjuvant activity.

IMMUNOTHERAPY: enhancement of an immune response by any one or more of a variety of adjuvants incorporating one or more antigens.

LIPOSOMES: synthetic lipid vesicles consisting of phospholipid bilayers surrounding one or more aqueous compartments. Antigens can be imbedded in the liposomes for induction of immune responses.

PLASMID: circular double standed DNA which, in vector form, is not bound to the chromosome.

PROMOTER: a region of DNA involved in the binding of RNA polymerase to initiate transcription.

VACCINE: a composition which produces active immunity. A vaccine is comprised of materials from microorganisms that contain antigens in an innocuous form with or without one or more adjuvants. The materials may comprise antigenic determinants and/or subunits from the microorganism and may be in the form of glycoproteins or proteins.

PROPHYLACTIC VACCINE: an active immunity inducing composition given to naive individuals to prevent or ameliorate primary infection and prevent the establishment of latent infection.

THERAPEUTIC VACCINE: an active immunity inducing composition given to individuals with latent or recurrent infection to reduce or minimize recurrences.

SYSTEMIC VACCINE: a composition for inducing active immunity relating to the entire individual as distinguished from any one individual area.

LOCAL VACCINE: a composition for inducing active immunity relating to one individual area as distinguished from the entire individual.

III. SUMMARY OF THE INVENTION

The purpose of this invention is to produce, by recombinant DNA techniques, an HSV glycoprotein or non-glycoprotein polypeptide, including but not limited to a gD-related, gB-related or Vmw65-related protein, which may be used as an immunogen in a vaccine to protect against HSV-1 and/or HSV-2 infections. Vaccines made from genetically engineered immunogens should be safer than conventional vaccines made from attenuated virus because there is no risk of infection to the recipient; and specifically with the herpes virus, there should be no risk of cervical cancer. Alternatively, the genetically engineered glycoprotein or protein product may be used to produce antibodies for use in passive immunotherapy.

Methods and compositions are therefore provided for the cloning and expression of an HSV glycoprotein or non-glycoprotein gene in single-cell host organisms. However, the present invention could be practiced in any cell line that is capable of the replication and expression of a compatible vector, including but not limited to, CHO and Vero cell lines. The invention is also intended to include expression vectors which serve equivalent functions as that described herein, and which become known in the art subsequently to this application. Also described are methods for culturing these novel single-cell organisms to produce the HSV gene product and methods for the purification of the gene product.

A human host is then preferably inoculated with a vaccine comprising an immunity inducing dose of one or more HSV glycoproteins or proteins of the invention by the systemic route, the enteric route or by ocular route. When administered by the ocular route, the vaccine can be given alone or in combination with systemic and/or enteric vaccination. The vaccine may also comprise one or more adjuvants administered with, before or after the glycoprotein component of the vaccine. Typically, one or several inoculations of between about 10–1000 μg each are sufficient to effect immunization of a human host.

The vaccine of the invention may be conveniently utilized in liquid form, freeze-dried, spray dried or lyophilized form, in combination with one or more suitable preservatives and protective agents to protect the glycoproteins or proteins during processing.

A. Antigens

The HSV-1 glycoproteins comprising the subject immunotherapy include but are not limited to glycoproteins gB, gC, gD, gE, gG, gH, gK, gL, gI, Vmw65, ICP0 and ICP4. The HSV-1 glycoproteins may be native, purified native, recombinant and/or synthetic. The recombinant glycoproteins may be obtained by the procedure set forth below, or any equivalent procedure. The vaccine may comprise one or more of these glycoproteins in a dose of 10–1000 μg per inoculation.

B. Adjuvants

Vaccines are often administered in an emulsion with various adjuvants. The adjuvants aid in attaining a more durable and higher level of immunity using smaller amounts of antigen in fewer doses than if the immunogen were administered alone. The adjuvants for use in the present invention include but are not limited to alum, Freund's, MTP-PE and ISCOMs (Quil A). In addition, the vaccine may comprise a liposome or other membrane bound vesicle comprising one or more HSV-1 glycoproteins administered with or without one or more adjuvants to induce the cell mediated immune response.

C. Immunization Routes

The ocular route is the preferred route of inoculation; however, this designation as the preferred inoculation route is not meant to preclude any other route of administration. The vaccine can be administered by the ocular route either alone or in combination with systemic (intramuscular or subcutaneous) and enteric vaccination. The ocular route includes but is not limited to subconjunctival injection, surface drops, a slow-release device such as a collagen shield, a hydrogel contact lens or an ALZA "Ocusert."

Subconjunctival vaccination is done using proparacaine for anesthesia prior to the injection of 0.2–0.5 ml of vaccine, in a dose of 10–1000 μg/inoculation, given in an insulin syringe and a small gauge needle. The injection is given in the lower cul-de-sac ensuring that the vaccine material remains subconjunctival and does not leak out.

The surface drops vaccination involves placing 50 μl of expressed glycoproteins with or without adjuvant in the conjunctival cul-de-sac and then rubbing the eye gently for 30 seconds while held closed. Since the expressed glycoprotein may be quickly cleared, the procedure should be repeated four times a day for five days to prolong the exposure, all of which comprise a single vaccination. For better retention, the tear drainage ducts may be temporarily blocked using collagen or other devices.

A collagen shield may also be soaked in a concentrated solution containing glycoproteins and adjuvant and then placed in the eye like a contact lens. The lid is then closed for several days by external application of medical grade cyanoacrylate adhesive, during which time the antigen is continuously released. Alternatively, the glycoproteins may be encapsulated in a microcapsule and then implanted into the eye to facilitate continuous antigen release.

C. Expression System For The Glycoproteins

Consistent high expression of the HSV-1 glycoproteins from the same source is an important factor in the development of a human HSV vaccine. Until recently, studies have been hampered by the diverse expression vectors and the diverse viral sources of the various HSV-1 glycoproteins expressed, making meaningful comparison among the expressed glycoproteins difficult. To overcome this problem, we have individually expressed high levels of seven HSV-1 glycoproteins from one virus strain in a single vector system as outlined in detail in Section V below.

The examples set forth below describe use of baculovirus, the polyhedron promoter system and insect cells as host cells. However, it would be well within the skill of the art to use analogous techniques to construct expression vectors for expression of desired glycoprotein and protein products in alternative host cell cultures.

D. Test Model

An important tool in the development of a human ocular HSV vaccine is the test animal model used. Our test system is the rabbit eye because HSV infections there very closely simulate what happens in the human eye. For instance, the severity of the eye disease is similar, latency is similarly established, and spontaneous reactivations occur much as they do in humans.

The invention relates generally to immunotherapy for the treatment of HSV infection in a human host. The invention also relates to the expression of high levels of high quality bioactive HSV-1 glycoproteins or proteins from one virus strain in a single vector system.

One aspect of the invention involves a systemic vaccine comprising one or more HSV-1 glycoproteins or proteins to decrease spontaneous HSV-1 shedding and to reduce the incidence of primary HSV-1 infection. Another aspect of the invention involves a local ocular therapeutic vaccine comprising one or more HSV-1 glycoproteins or proteins to decrease spontaneous HSV-1 ocular shedding and thereby control recurrent corneal disease. Another aspect of the invention involves a local ocular prophylactic vaccine comprising one or more HSV-1 glycoproteins or proteins to reduce the incidence of primary HSV-1 infection.

It is therefore a general object of the present invention to develop effective immunotherapy for the treatment of HSV in a host.

It is an object of the present invention to develop effective systemic immunotherapy for the treatment or prevention of HSV in a human host.

It is an object of the present invention to develop effective local immunotherapy for the treatment of ocular HSV in a human host.

It is also an object of the present invention to develop a local therapeutic ocular vaccine to decrease spontaneous HSV ocular shedding and to control recurrent disease in a human host.

It is a further object of the present invention to develop a local prophylactic ocular vaccine to reduce the incidence of primary HSV infection in a human host.

It is still further an object of the invention to utilize an animal test model that closely simulates HSV infection in the human eye.

It is another object of the present invention to individually express high levels of the seven HSV-1 glycoproteins from one virus strain in a single vector system.

These and other objects will become readily apparent to those skilled in the art from the following description and appended claims.

IV. BRIEF DESCRIPTION OF THE DRAWINGS

The present invention will be described in connection with the accompanying drawings in which.

FIG. 3 is a Southern Blot analysis of recombinant baculovirus DNA; a. Ethidium bromide staining gel; b. Autoradiogram; M. markers (IKb); P. plasmid-BamHI cut pAc-gD1 transfer vector; B. baculovirus recombinant BamHI cut DNA. Arrows indicate the location of the BamHI released gD structural gene from the initial vector (pAc-gD1) and from the recombinant baculovirus (vAc-gD1).

Figure 4:
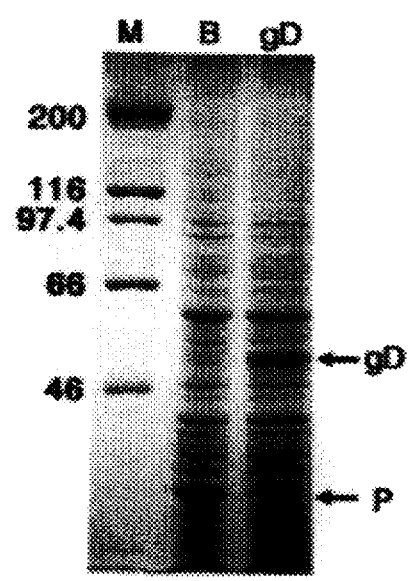

FIG. 4 is a coomassie blue staining of recombinant baculovirus infected cell extracts following SDS-PAGE. M. molecular weight markers; B. wild type baculovirus infected cells; gD.vAc-gD1. The arrows on the right indicate the positions of the major glycosylated gD band in gD and the wild type polyhedron protein visible in B.

Figure 5:
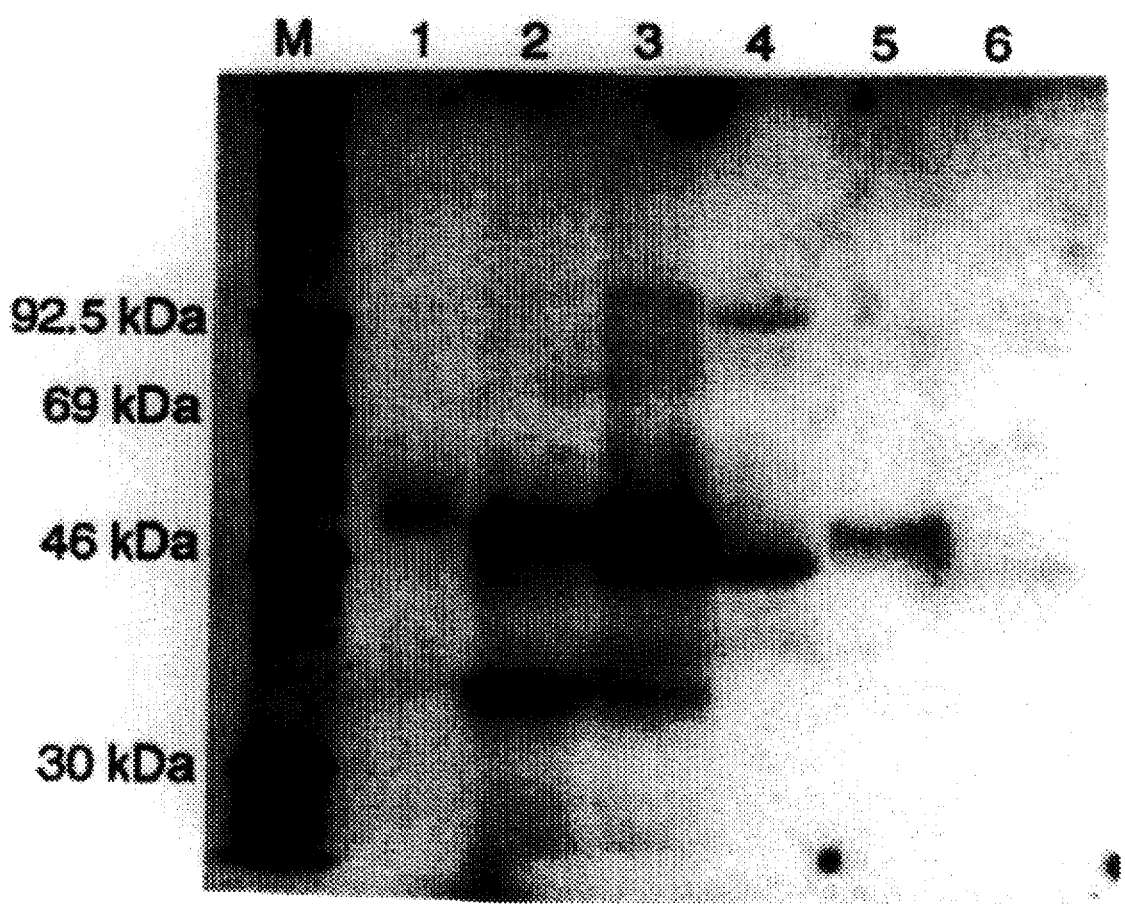

FIG. 5 is a Western Blot analysis of baculovirus expressed gD glycosylation. M. molecular weight markers; 1. Veto cells infected with HSV-1 at an MOI of 10 for 24 hr.; 2. vAc-gD1 infected cells at 48 hr.; 3. vAc-gD1 infected cells at 72 hr.; 4. Tunicamycin treated vAc-gD1 infected cells; 5. Endo-H treated vAc-gD1 infected cells; 6. Endo-F treated vAc-gD1 infected cells.

Figure 6A:
Figure 6B:
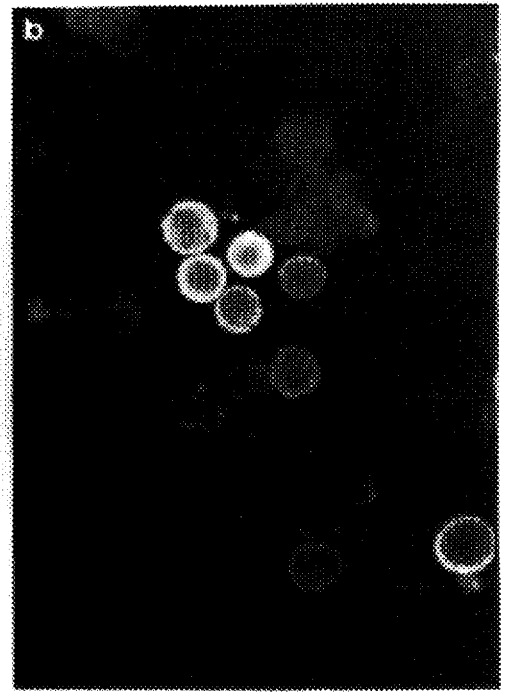
Figure 6C:
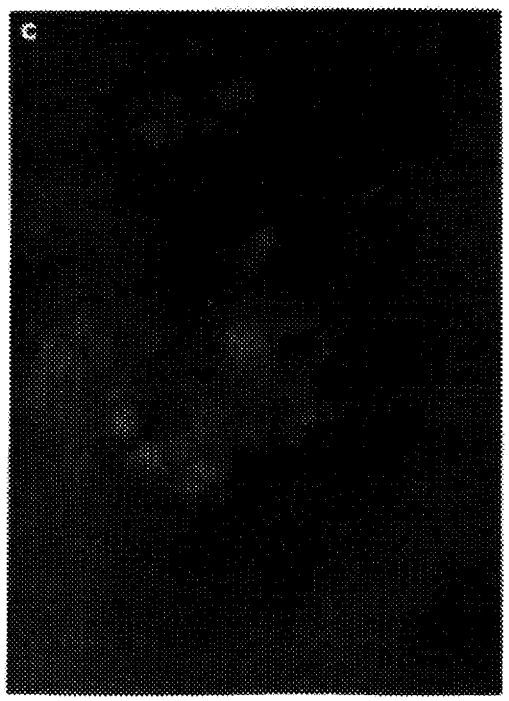

FIGS. 6A, 6B, & 6C show the immunofluorescence of recombinant baculovirus-infected cells. a. Recombinant vAc-gD1 infected cells, total fluorescence; b. vAc-gD1 infected cells, surface fluorescence; c. wild type baculovirus infected cells, total fluorescence.

V. DETAILED DESCRIPTION OF THE INVENTION

The present invention utilizes recombinant DNA techniques to insert a DNA sequence coding for an HSV-1 glycoprotein, protein or a portion thereof, into a DNA vector, such that the vector is capable of replicating and directing expression of the glycoprotein or protein gene in a foreign host. The resulting recombinant DNA molecule is introduced into insect cells to enable high production of the glycoprotein, or protein, or a portion or molecular variant thereof by the host cells. The glycoprotein or protein produced is then isolated and purified for use in immunotherapy against both HSV type 1 and type 2.

A. Preparation Of HSV-1 Glycoproteins

It is to be understood that other procedures may be utilized and that changes may be made without departing from the scope of the invention. The following detailed description is, therefore, not to be taken in a limiting sense, and the scope of the present invention is best defined by the appended claims.

1. Baculovirus expression of HSV-1 gD

The DNA sequence encoding the complete herpes simplex virus type 1 (HSV-1) glycoprotein D (gD) was inserted into a baculovirus transfer vector under control of the polyhedron gene promoter of the baculovirus *Autographa californica* nuclear polyhedrosis virus (AcNPV). After co-transfection of *Spodoptera frugiperda* (Sf9) insect cells with wild-type AcNPV DNA and the recombinant transfer vector DNA, polyhedron-negative recombinants that expressed high levels of HSV-1 gD were isolated using immunoaffinity selection with antibody coated magnetic particles followed by plaque purification. These recombinant baculoviruses expressed a protein that was slightly smaller than virion HSV-1 gD made in Vero cells. The HSV-1 gD recombinant protein was expressed at high levels, was glycosylated, was found on the membrane of Sf9 cells, and reacted with gD specific antibodies. The procedure is described in detail (12) as follows:

a. Materials and methods i. Viruses and cells

The E2 strain of *Autographa californica* nuclear polyhedrosis virus (AcNPV) (baculovirus) and *Spodoptera frugiperda* clone 9 (Sf9) insect cells were gifts from Dr. Max Summers, Texas A & M. Insect cells were grown in TNM-FH media (13) containing 10% fetal bovine serum. Wild-type and recombinant baculoviruses were grown according to the procedures of Summers and Smith (13). Plaque purified HSV-1 (strains McKrae and KOS) and Vero cells were grown using standard techniques as previously described (14).

ii. Construction of AcNPV recombinant transfer vector

Plasmid pSS17 (HSV-1 strain KOS, a gift from D. C. Johnson, Ontario, Canada) was double digested with Afl II/Mae I and the 1.2 kb fragment containing the complete coding region of gD was isolated and blunt ended into the Hinc II site of pGEM3 (see FIG. 1). The construct was linearized with Hind III, digested briefly with Bal 31 exonuclease to remove unwanted nucleotides upstream from the first ATG in the coding sequence, and BamHI linker was added. The resulting fragment was isolated and ligated into the unique BamHI site of the vector pAcYM I (15) in lieu of the polyhedron structural gene (under control of the strong polyhedron gene promoter). Partial sequence analysis indicated that the cloned gD has a short noncoding region of 6 nucleotides at the 5' end. No HSV noncoding sequences are present after the termination codon (TAG) at the 3' end.

iii. Preparation of magnetic particles for selection of recombinant gD

Ten ml of magnetic goat-anti rabbit IgG (Advanced Magnetics Inc., Cambridge, Mass.) were transferred to a 75 ml tissue culture flask. A large magnet (supplied by the manufacturer) was placed on one flat surface of the flask to attract and retain the magnetic goat anti-rabbit IgG and the supernatant was decanted and discarded. After washing the magnetic material with coupling buffer (100 mM PBS pH 7.4, 0.1% BSA, 0.1% non-fat dry milk, and 1 mg/ml AcNPV total protein extract) 1 ml of gD polyclonal antibody (40 μg) in 9 ml coupling buffer was added to the BioMag (magnetic goat anti-rabbit IgG). The mixture was agitated overnight at 4° C., and then magnetically separated. After two successive washes with coupling buffer and two washes with TNM-FH, the BioMag-gD antibody complexes were resuspended in 10 ml TNM-FH and stored at 4° C.

iv. Transfection and selection of recombinant viruses

Sf9 cells were cotransfected with purified infectious AcNPV DNA and pAc-gD 1 plasmid DNA essentially as described (13). After four days of incubation at 28° C. and the appearance of CPE, the infected cells were screened by immunoaffinity selection. The cell pellet was harvested and incubated with 1 ml of anti-gD antibody-coated magnetic particles and 1 ml of media for 60 minutes on ice. The cell suspension was magnetically separated, fresh media was added to the magnetically collected cells and separation (washing) was repeated five times at room temperature. The selected material was used to infect confluent monolayers of Sf9 cells. Following viral growth the supernatant was titrated on confluent monolayers of Sf9 cells. Plaques exhibiting no evidence of occlusion bodies (viral polyhedra) as determined by transmission light microscopy were recovered and retitered on Sf9 cells to obtain recombinant, polyhedron-negative viruses. Following a third plaque picking, high titered stocks ($10^7$–$10^8$ PFU/ml) of recombinant viruses were obtained.

v. Preparation of viral DNA

Sf9 cells were infected with recombinant virus at a multiplicity of 10 PFU/cell and incubated at 28° C. for 27 hours. The infected cells were freeze-thawed and centrifuged for 10 minutes at 1000×g to remove cell debris. The procedures used for virus isolation and viral DNA extraction (from the supernatant fluid) and blotting have been previously described (16).

vi. Western blots

Western immunblot analyses were carried out under denaturing conditions. Samples for SDS-PAGE were disrupted in electrophoresis sample buffer containing 2% SDS and 10% 2-mercaptoethanol and heated at 100° C. for three minutes. Proteins were separated by SDS-PAGE (17), and transferred to nitrocellulose paper by electrophoresis as described by Towbin et al. (18). After transfer, nitrocellulose blots were blocked in BLOTTO (5% nonfat dry milk in PBS) and then reacted with anti-gD polyclonal antibody or total HSV-1 antibody 1 hour at 4° C. Bound antibody was detected by reacting the blots with $^{125}$I-protein A for 1 hour at 25° C. followed by autoradiography.

vii. Endoglycosidase H and endoglycosidase F

To determine if complex sugars were added as part of the gD glycosylation protein, Endoglycosidase H (Endo-H) and Endoglycosidase F (Endo-F) treatments were done on lysed infected cells as described by the manufacturer (Boehringer Mannheim Biochemicals). Endo-H removes high mannose chains while Endo-F removes both high mannose and hybrid sugars.

viii. Tunicamycin treatment

To determine if the expressed gD underwent N-glycosylation, infected cell monolayers were treated with 4 µg/ml tunicamycin (an inhibitor of asparagine-linked glycosylation) in TNM-FH media for 48 hours as described (19).

ix. Immunofluorescence

Sf9 cells were infected with wild-type AcNPV or recombinant baculoviruses expressing gD at a multiplicity of infection of 10 PFU/cell and incubated for 72 hours. To look at total fluorescence, cells were washed with PBS, fixed with acetone and anti-gD polyclonal antibody (provided by Dr. Richard Eberle) was added and incubated for 1 hour at 37° C. Alternatively, to determine cell surface immunofluorescence, unfixed, unpermeabilized cells were washed with PBS and incubated with antibody for 1 hour at 4° C. After washing, slides were fixed with acetone. Slides for total and surface fluorescence were then washed with PBS, stained with fluorescein-conjugated goat anti-rabbit IgG antibody for 1 hour at 37° C., washed again with PBS, and examined for fluorescence.

2. Results a. Construction of recombinant viruses expressing gD

Figure 1:
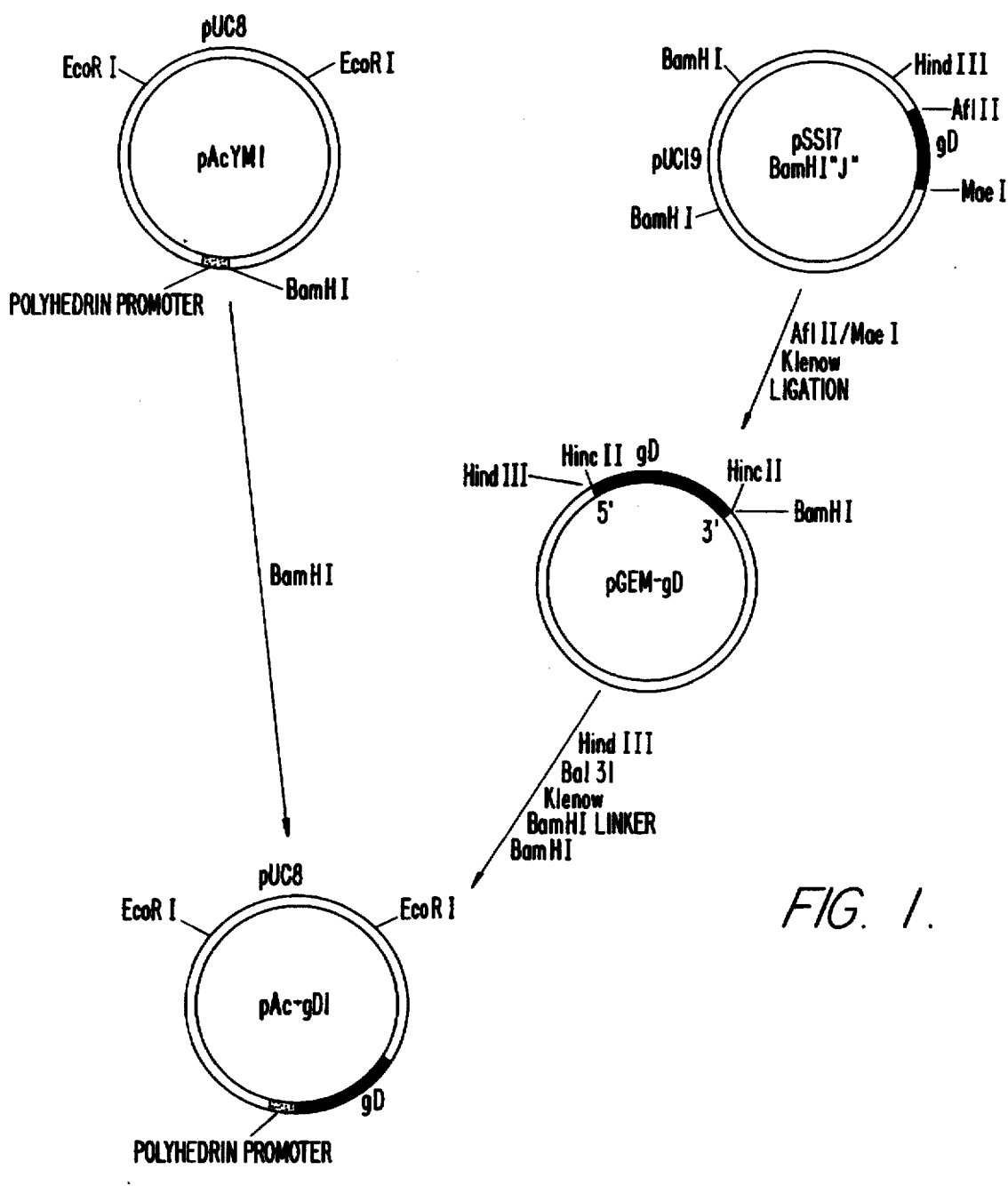
FIG. 1 is a schematic diagram of the construction of plasmid pAC-gD1 used in constructing exemplary recombinant virus strains of the invention.

The strategy for the construction of the baculovirus transfer vector containing the complete gD open reading frame from HSV-1 is shown in FIG. 1. A complete DNA copy of the gD gene from the BamHI J fragment, was isolated by restriction enzyme digestion with AflII/MaeI. Most of the 5' noncoding sequences were removed by Bal31 digestion. The resulting DNA was then inserted into the BamHI site of the pAcYM1 vector (FIG. 1). As confirmed by restriction enzyme analysis and partial sequencing, this construct contains the entire sequence of the gD gene. It has a non-coding region of only 6 nucleotides in front of the first ATG. This is followed by the complete coding region of 1182 nucleotides. To transfer the gD gene into the baculovirus AcNPV genome, Sf9 cells were cotransfected with pAc-gD1 DNA and infectious AcNPV DNA. Putative recombinant viruses were enriched by immunoaffinity selection, which was followed by three cycles of polyhedron-negative plaque purification. In this study, one round of immunoselection increased the efficiency of obtaining recombinant viruses by several fold with yields of better than 8% recombinants in the first plaque purification cycle.

b. Western blot analysis

Figure 2:
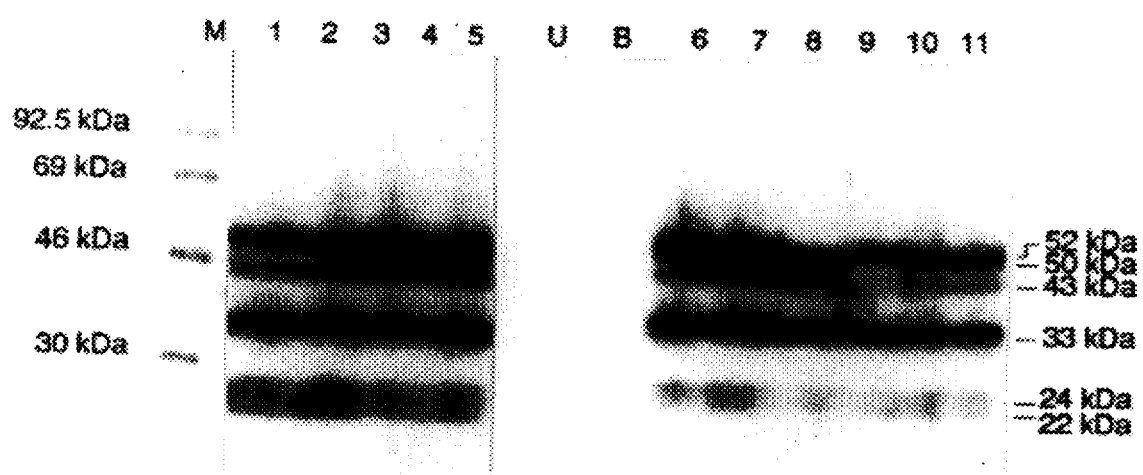
FIG. 2 is a Western Blot analysis of eleven recombinant baculoviruses expressing HSV-1 glycoprotein in insect cells. Lane M represents molecular weight markers.

Confluent monolayers of Sf9 cells were infected at a multiplicity of 10 PFU/cell with 11 individual recombinant baculoviruses obtained after three plaque purifications and total protein extracts were analyzed by Western blotting. Our vAc-gD1 recombinants produced 6 protein bands that reacted with both total HSV-1 polyclonal antibody (FIG. 2) and gD polyclonal antibody (FIG. 5). A band with an apparent molecular weight of 43 kDa corresponds to the non-glycosylated primary gD polypeptide that has a predicted molecular weight of 43,291 Da. Two larger bands (50 kDa and 52 kDa) ran as a very tight doublet that was not resolved in this blot. These two bands presumably represent the partially glycosylated precursor pgD and mature gD (20, 21) respectively.

The three smallest bands had apparent molecular weights of 33, 24, and 22 kDa. A similar pattern of bands was obtained with immunoaffinity column (Affi-Gel 10; Bio-Rad) purified gD (using gD monoclonal antibody, a gift from Dr. D. Wiley).

Western blot analysis of recombinant infected cell medium did not detect any gD. This suggests that the expressed gD is retained in the cell or in the cell membrane as with HSV-1 infected cells and is not secreted into the medium.

c. Southern blot analysis

Figure 3A:
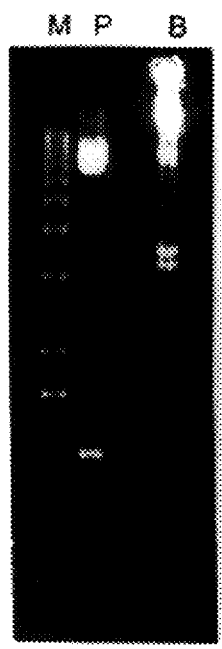
Figure 3B:
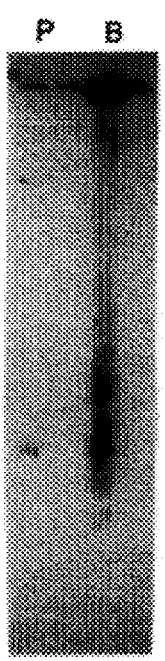

Since no obvious differences in the expression levels or the sizes of any of the gD related bands were seen among the 11 recombinant viruses, one recombinant virus was arbitrarily selected for subsequent study and designated vAc-gD1. To verify the presence of full length HSV-1 gD DNA in vAc-gD1, the baculovirus DNA was digested with the restriction enzyme BamHI and Southern blots were done using the gD gene as a probe (FIG. 3). As can be seen by both ethidium bromide staining of the DNA (FIG. 3a) and Southern analysis using a gD specific probe (FIG. 3b), BamHI digestion of the gD recombinant generated a band of the expected size (approximately 1.2 kb). This corresponds to the HSV-1 gD gene cloned into the expression vector (FIG. 3).

d. Visualization of expressed gD by SDS-PAGE and coomassie blue staining

Total cell extracts from wild type baculovirus and vAc-gD1 recombinant baculovirus infected cells were run on SDS-PAGE and protein bands were stained with coomassie blue. The polyhedron protein band seen in wild type baculovirus infected cells (FIG. 4, lane B) was missing in vAc-gD1 infected cells, while a new, larger band of similar intensity was present in the vAc-gD1 infected cells (FIG. 4, lane gD). Neither band was seen in uninfected cells. This new recombinant band had an apparent molecular weight of approximately 50–52 kDa, corresponding in size to the tight doublet upper bands seen by Western analysis (FIG. 2, bands 50 and 52 kDa), and represented the major expressed gD species in this recombinant baculovirus.

Visual observation of the stained gel suggested that the amount of expressed gD was similar to the amount of polyhedron in wild type baculovirus infected cells (FIG. 4, compare gD to P in lanes gD and B). To confirm this and to more accurately estimate the relative expression level of gD, the coomassie blue stained gel shown in FIG. 4 was scanned on a laser densitometer. The area under the combined peak representing gD and pgD was similar to the area under the peak for the polyhedron protein in wild type baculovirus infected cells. Identical results were obtained in scans of additional gels. Since the polyhedron protein has been estimated to comprise up to 40% of total cellular protein, this analysis indicates that the recombinant gD is expressed at very high levels (22).

e. Glycosylation of gD

To confirm that the expressed gD underwent glycosylation, tunicamycin treatment was done to prevent N-glycosylation in infected Sf9 cells. Infected cells were treated with 4 μg tunicamycin/ml of TNM-FH media from 0–48 h post infection, and total cell extracts were analyzed by Western blots using polyclonal anti-gD antibody. The tunicamycin treatment (FIG. 5, lane 4) reduced the apparent size of gD relative to the control (lanes 2 and 3). This result indicates that like native gD, the untreated expressed gD was glycosylated and contained N-linked sugars.

To determine if the expressed gD contained complex sugars, vAc-gD1 infected cell lysates were treated with Endoglycosidase-H (Endo-H, removes high mannose sugars) or Endoglycosidase-F (Endo-F, removes high mannose and hybrid sugars). As seen in FIG. 5 lane 5, gD was partially resistant to digestion by Endo-H. In contrast, Endo-F digestion decreased the apparent molecular weight of gD to approximately 45 kDa (FIG. 5, lane 6). Thus, similar to native gD, the expressed gD was partially resistant to Endo-H and susceptible to Endo-F. Therefore, like native gD the recombinant gD was glycosylated and contained N-linked hybrid sugars.

f. Immunofluorescence of recombinant gD in insect cells

To determine whether the expressed gD was transported to the cell surface, vAc-gD1 infected Sf9 cells were examined by indirect immunofluorescent antibody staining using polyclonal antibody to gD. Immunofluorescence was readily observed in recombinant-infected cells (FIG. 6a). No immunofluorescence was seen in cells infected with AcNPV (FIG. 6c) or in uninfected Sf9 cells. To look specifically for gD on the cell surface, indirect immunofluorescent antibody staining was done on cells prior to fixation (and permeabilization) (FIG. 6b). The surface fluorescence on vAc-gD1 infected cells was strong and comparable to that observed for permeabilized fixed cells. This indicates that the expressed gD was correctly transported to and anchored in the cell surface.

3. Baculovirus expression of HSV-1 gB, gC, gE, gG, gH or gI

Glycoproteins gB, gC, gE, gG, gH and gI (McGeoch et al., Journal of General Virology 69:1531–1574(1988)) were similarly expressed in baculovirus (23–28). In all cases, high level expression of a protein similar in size to the native glycoprotein was obtained. All the expressed glycoproteins were glycosylated, reacted with the appropriate monoclonal or polyclonal antisera, and were correctly transported to the cell surface.

B. Vaccination

1. Outline of Vaccine Trial

Rabbits. New Zealand White (NZW) male rabbits (approximately 2 kg each) are used for all experiments. As discussed above, these animals develop a primary and recurrent ocular herpetic disease that mimics HSV keratitis in man.

Virus and vaccines. McKrae, a highly pathogenic stromal disease causing HSV-1 strain, with a very high spontaneous reactivation rate is used for establishment of latency. Strain RE or W will be used in some experiments to confirm that results are not strain specific.

Day 0: Ocular infection for establishment of latency. Rabbits are bilaterally infected by placing $2 \times 10^5$ PFU (McKrae) into the conjunctival cul-de-sac, closing the eye, and rubbing gently for 30 seconds. Although this dose of virus results in the death of approximately 30% of the rabbits, this is the lowest dose at which all survivors become latently infected in both eyes (really both trigeminal ganglia). Although latency cannot be judged at this point without the loss of the rabbit for the vaccine experiment, our extensive experience indicates that virtually every trigeminal ganglia harbors HSV-1 latency under these conditions. At the termination of the vaccine trial, the trigeminal ganglia from those eyes that have not shown spontaneous or induced reactivation will be removed and explant co-cultivation done to confirm that latency had been established. In our experience this strain and dose combination results in the highest number of known latently infected and spontaneously reactivating eyes, (starting with a given number of rabbits) thus using the fewest possible rabbits. Also with this regimen, no more than 1% of rabbits become blind in both eyes (these rabbits are immediately sacrificed).

Subconjunctival vaccination is done using topical propacaine for anesthesia prior to subconjunctival injection of 0.2–0.5 ml of vaccine given with an insulin syringe and a small gauge needle. The injection is given in either the upper or lower cul de sac making an effort that the vaccine material remains subconjunctival and does not leak out.

Enteric vaccination is done by gavage down the rabbits throat.

Vaccination by surface drops and collagen shield is as described above.

Glycoprotein purification. Glycoproteins will be purified by differential centrifugation of freeze-thawed or detergent disrupted cell extracts, followed by immunoaffinity purification through columns with covalently bound HSV-1 antibody.

ISCONs with Quil-A are made as previously described in the literature (29, 30).

Day 21: Latency is considered to be established in all survivors (see Specific methods below for a discussion). Rabbits are randomly divided into trial and control groups and vaccinated ocularly.

Day 35: Vaccination repeated.

Day 49–118: Tear films are collected once a day, 5 days a week to look for spontaneous shedding indicative of HSV reactivation.

Day 49–118: Eyes are examined 3×/week (prior to tear film cultures) by slit lamp biomicroscopy to directly monitor epithelial keratitis, stromal disease and scarring.

Ocular parameters. Severity of ocular disease is scored on a 0 to 4 scale in a masked fashion by examination with slit lamp biomicroscopy using 1% methylene blue to delineate epithelial ulceration. Iritis and stromal keratitis are also scored on a 0 to 4 scale.

In vivo reactivation is done by iontophoresis with 6-hydroxydopamine followed by topical epinephrine (31).

Blood and tear samples are taken for immunological analysis prior to initial infection (day 1), prior to vaccinations (days 20 and 34), 2 weeks after the second vaccination (day 49), and at the end of the experiment (>day 118).

In vivo reactivation. Co-cultivation of trigeminal ganglia is done as previously described (32).

Serum neutralizing antibody titers are done by plaque reduction assays (33).

Local ocular sIgA and IgG titers are done using tears collected on a "sno strip" (34) for human sIgA cervical HSV-2, with adjustments made to detect rabbit (rather than human) HSV-1 (rather than HSV-2) specific sIgA and IgG. Correlations between IgG and IgA neutralization titers and ELISAs will be done.

Systemic IgA and IgG titers are done from sera by ELISA (35).

Lymphocyte proliferation responses will be monitored by checking for T cells that will proliferate upon stimulation with HSV proteins (36). Peripheral blood mononuclear cells (PBMC) are collected from latently infected, latently infected immunized, and control rabbits by venipuncture into preservative-free heparinized syringes, with subsequent purification by Ficoll-hypaque centrifugation. PBMC are resuspended to a concentration of $2.5 \times 10^5$ cells/ml in RPMI-1640 medium containing 15% heat-inactivated fetal bovine serum and antibiotics (RPMI-15% FBS). 200 µl of PBMC ($5 \times 10^4$) is added to each of four replicate round bottom microtiter plate wells, followed by the addition of 100 µl of 1.0 or 5.0 µg/ml solutions of expressed HSV-1 glycoprotein, 100 µl of UV-light inactivated HSV-1 ($10^6$ PFU/ml prior to UV irradiation), or 100 µl of RPMI-15% PBS as a control. Seven days after the onset of stimulation, 1 µCi of [$^3$H] thymidine ([$^3$H]TdR, NEN, Boston, Mass.) is added for the last 6 hours of incubation at 37° C. Cells are then harvested by using a multiple well harvesting device, and [$^3$H]TdR incorporation determined by liquid scintillation counting.

Therapeutic effectiveness is determined by comparing ocular shedding, recurrent epithelial keratitis, recurrent stromal keratitis, and scarring to mock vaccinated controls. All animal work and analyses will be masked to eliminate bias.

2. Controls

All vaccine trials were compared to a mock vaccine for the amount of ocular shedding, the amount of recurrent stromal disease and the levels of immune response.

Spontaneous Ocular Shedding as a Valid Predictor of Corneal Lesions

Corneal epithelial lesions and stromal scarring are usually preceded by detectable levels of ocular HSV shedding. Hence, shedding is almost certainly a prerequisite for recurrent epithelial and stromal lesions. All else being equal, it was surmised that a decrease in shedding, i.e., less culture-detectable infectious virus in tears, will result in decreased corneal disease. Ocular shedding was therefore determined by collecting tear films once a day, five days per week from each eye and culturing them for infectious virus between day 49 (two weeks after the final vaccination) and day 118.

4. Induced Ocular Shedding

Induced ocular shedding can be accomplished by iontophoresis with 6-hydroxydopamine followed by topical epinephrine as described previously in the literature.

5. Selection of Vaccines

Various combinations and permutations of the seven HSV-1 glycoproteins or proteins can be made and used. Among these combinations include HSV-1 gD and gB, a combination of all seven HSV-1 glycoproteins in equimolar amounts, and any combination of one or more of the seven HSV-1 glycoproteins and proteins.

6. Adjuvants

MTP-PE is the adjuvant of choice for subconjunctival vaccinations. MTP-PE may be administered with the HSV-1 glycoproteins alone or in combination with other adjuvants. MTP-PE may also be encapsulated in a liposome in combination with one or more HSV-1 glycoproteins or proteins. The use of other adjuvants, known or yet to be discovered, however, is not foreclosed by the disclosure of MTP-PE as the preferred adjuvant.

For systemic vaccination, i.e. intramuscular (IM) or subcutaneous (SC) vaccination, the most powerful adjuvants may be used. These include, but are not limited to, alum, Freund's complete, Freund's incomplete, MTP-PE, ISCOMs (Quil A), and any combination of these.

EXAMPLE 1

Systemic Therapeutic Vaccination with recombinant HSV-2 gB-gD

Methods

Thirty-six NZW rabbits with culture proven binocular HSV-1 McKrae infection were given subcutaneous vaccinations (0.5 ml) of Chiron gB2 and gD2 with MTP-PE adjuvant on days 21 and 39 post infection. The mock vaccinated group received tissue culture media pursuant to the same schedule. Daily 7 day/wk swab cultures (primary rabbit kidney) were taken for 36 days beginning 3 weeks after the second vaccination. All positive cultures were confirmed by neutralization. ELISA titers (capture Ag purified KOS) were done on blood samples taken 5 weeks after the second vaccination (sera were diluted in ½ log steps from 1/100 to 1/300,000). Daily 5 day/wk slit lamp biomicroscopy was done over the same period.

Results

TABLE 1

Spontaneous ocular shedding and dendritic positive eyes, following systemic vaccination.

| Vaccine & Adjuvant | Route | # Animals/ # Eyes | + Culture | % Positive | # Dendritic | % Dendritic |
|---|---|---|---|---|---|---|
| Chiron gB2 + gD2 with MTP-PE | Subcutaneous | 19/38 | 124/1368 | 9.6% | 121/1140 | 1.93% |
| Mock without adjuvant | Subcutaneous | 17/34 | 151/1224 | 12.34% | 19/1020 | 1.86% |

*all eyes cultured for 36 consecutive days
**slit lamp biomicroscopy (5 days/wk) for 30 days As illustrated in Table 1, there is no significant difference in the number of positive cultures or the number of eyes with dendritic figures between the mock and the Chiron vaccinated groups. There is also no difference in (data not shown) (1) the number of eyes that have 1 or multiple recurrences; (2) the number of rabbits that have 1 or multiple recurrences; (3) the average duration of shedding events; (4) the severity of keratitis; or (5) the HSV-1 ELISA titer in high vs. low recurrence animals, although the average titer is slightly higher in the Chiron than the mock vaccinated group. There was no difference in long term scarring and no signs of ocular toxicity.

Although there was no increase in shedding or dendritic keratitis produced by systemic vaccination with gB2+gD2 with MTP-PE, neither was any significant decrease seen in the same parameters with the same systemic subunit vaccine. Consequently, systemic vaccination does not produce adequate ocular protection from HSV-1 recurrences.

EXAMPLE 2

Systemic Vaccination with HSV-1 gD

Methods

V52, a genetically engineered vaccine virus recombinant that expresses the HSV-1 glycoprotein gD (obtained from B. Moss) was used to vaccinate rabbits intradermally. It should be noted, however, that the HSV-1 gD may also be obtained from the procedures described above or any equivalent. Significant HSV-1 neutralizing antibody titers were produced, although they were not as high as those induced by vaccination with live HSV-1. The mock vaccinated group received a vaccinia-influenza recombinant, V36. The positive control group received live attenuated HSV-1 virus (KOS) subcutaneously. Rabbits were challenged ocularly with topical application of $2 \times 10^5$ PFU of HSV-1 McKrae.

Eyes were monitored for 35 days for epithelial keratitis, stromal keratitis, and iritis.

Results

V52 gD provided a small amount of protection against HSV-1 induced epithelial keratitis (p=0.02) and long term stromal scarring (p=0.04). In addition, 89% of the V36 vaccinated rabbits (negative control) could be induced to reactivate. In contrast, only 55% of the V52 vaccinated rabbits could be induced to reactivate, suggesting a modest protective effect. The positive control rabbits vaccinated subcutaneously with KOS produced the same results as seen with gD. Hence, systemic vaccination with HSV-1 gD on live attenuated KOS HSV-1 did not produce adequate ocular protection from HSV-1 recurrences.

EXAMPLE 3

Local ocular vaccination with KOS

Methods

Twelve NZW rabbits were vaccinated with the non-pathogenic live HSV-1 strain, KOS. KOS replicates very well in the eye, however, even at extremely high titers, the KOS strain causes minimal eye disease in the rabbit. The rabbits were vaccinated by placing $5 \times 10^8$ virus in each eye and holding the eye closed for 30 seconds. A control group of 12 rabbits were each mock infected with tissue culture media. Four weeks later, the rabbits were challenged with HSV-1 McKrae and the eyes were observed by slit lamp biomicroscopy over a 2 week period. The severity of disease was scored on a scale of 0–4.

Results

Maximum eye involvement occurred on day 7, the average severity of disease is shown in Table 2.

TABLE 2

Ocular vaccination protects against primary ocular infection.

|  | EYE Mock vaccinated | EYE KOS vaccinated | SYSTEMIC McKrae Vaccinated |
| --- | --- | --- | --- |
| Epithelial keratitis | 1.4+/−0.5 | 0.0 | 2.1+/−1.2 |
| Stromal keratitis | 2.0+/−0.5 | 0.0 | 1.9+/−1.0 |
| Iritis | 2.1+/−1.7 | 0.1+/−0.05 | 1.5+/−1.4 |

*McKrae data is from the V52 experiment described above.

As demonstrated above, the protection afforded against ocular challenge at 4 weeks was almost complete. Ocular vaccination was dramatically more efficient than the systemic vaccination demonstrated in Examples 1 and 2 above. This experiment therefore suggests that a local ocular vaccine may afford the necessary protection in the rabbit against ocular challenge that is lacking with systemic vaccination. Moreover, since ocular vaccination appears more powerful in protecting against primary ocular infection, it follows then that it is also likely to be more powerful in protecting against ocular recurrence. Because the rabbit ocular model of HSV infection mimics the human infection, local ocular vaccination also appears to represent the best protection from HSV-1 ocular recurrences in humans.

EXAMPLE 4

Local Ocular Vaccination with Expressed HSV-1 gB and gD

Methods

Five NZW rabbits with culture proven binocular HSV-1 McKrae infection were given subconjunctival vaccinations on days 32 and 54 post infection. The vaccine comprised equal amounts of expressed gB1 and gD1 mixed 50/50 with MTP-PE adjuvant. Nine eyes were vaccinated: 4 animals bilateral, 1 unilateral. Daily 7 day/wk swab cultures (primary rabbit kidney) were taken for 22 days beginning 3 weeks after the second vaccination. All positive cultures were confirmed by neutralization. Daily 5 day/wk slit lamp biomicroscopy was carried out over the same period.

Results

There were no corneal or anterior chamber abnormalities seen on biomicroscopy that differed from the mock vaccinated animals. All eyes showed mild generalized infection for 1 week following subconjunctival vaccination. Three eyes showed sustained localized mild conjunctival infection at the vaccination site.

The results shown in Table 3 below are intriguing and suggest reduced shedding following ocular subconjunctival vaccination with gB1+gD1. These experiments demonstrate that (1) local conjunctival vaccination is possible without apparent harm to the recipients; and (2) local ocular vaccination is more effective then systemic vaccination in preventing HSV ocular recurrences.

TABLE 3

Spontaneous ocular shedding and dendritic keratitis following local subconjunctival vaccination with baculovirus expressed HSV-1 gB and gD.

| Vaccine & Adjuvant | Route | # Animals/ # Eyes | + Culture | % Positive | # Dendritic | % Dendritic |
| --- | --- | --- | --- | --- | --- | --- |
| gB1 + gD1 with MTP-PE | Local subconjunctival | 5/9 | 9/198 | 4.55% | 2/126 | 1/59% |
| KOS without Adjuvant | Systemic suncutaneous | 17/34 | 75/748 | 10.02% | 11/476 | 2.31% |

*all eyes cultured for 22 consecutive days-KOS numbers are reported for the days that the subconjunctival animals were cultured, i.e. Days 77–99 post infection.
**slit lamp biomicroscopy (5 days/wk) for 14 days In summary, the Examples above illustrate that: 1) systemic vaccination with HSV-2 gB+gD with MTP-PE did not produce adequate ocular protection from HSV-1 recurrences; 2) systemic vaccination with HSV-1 gD or live attenuated KOS HSV-1 also did not produce adequate ocular protection from HSV-1 recurrences; 3) local ocular vaccination with a live nonpathogenic HSV-1 strain did protect against primary ocular infection; and 4) local ocular vaccination with HSV-1 gB and gD was effective in preventing HSV ocular recurrences. These examples illustrate that a local ocular immunogenic comprised of one or more HSV-1 glycoproteins or proteins, would greatly alleviate HSV ocular recurrences, the most frequent serious viral eye infection in humans in the United States and a major cause of viral induced blindness in the world.

The foregoing detailed description is given for clearness of understanding only, and no unnecessary limitations are to be understood or inferred therefrom, as modifications within the scope of the invention will be obvious to those skilled in the art.

BIBLIOGRAPHY

1. Nesburn, A. B., *Report of the corneal disease panel: Vision Research: A national plan 1983–1987*. Vol. II, part III, edited by Nesburn, A. B., St. Louis, Mo.
2. Klein, R. J., Reinfections and site-specific immunity in herpes simplex virus infections. *Vaccine*, 7:380–381 (1989).
3. Stanberry, L. R. et al., Herpes simplex virus glycoprotein treatment of recurrent genital herpes. *J. Infec. Dis.*, 157:156–63 (1988).
4. Kern, A. B. et al., Vaccine Therapy in Recurrent Herpes Simplex, *Arch. Derm.*, 89:844–845 (1964).
5. Frenkel, L. et al., A randomized double blind, placebo-controlled phase 1 trial of a herpes simplex virus purified glycoprotein (gD1) vaccine. *Interscience Conf. on Antimicrobial Agents & Chemo.*, 206 (1990).
6. Betman, P. W. et al., Efficacy of Recombinant Glycoprotein D Subunit Vaccines on the Development of Primary, Recurrent, and Latent Genital Infections With Herpes Simplex Virus Type 2 in Guinea Pigs. *J. Infec. Dis.*, 157(5):897–902 (May 1988).
7. Blacklaws, B. et al., Immunogenicity of herpes simplex type 1 glycoproteins expressed in vaccinia virus recombinants. *Virology*, 177:727–736 (1990).
8. Spear, P. G., Glycoproteins specified by herpes simplex virus. In: *The herpesviruses*, edited by Roizman, B., New York, Plenum Press, pp. 315–356 (1985).
9. Narrild, B., Humoral response to herpes simplex virus infections. In: *The herpesviruses*, edited by Roizman, B., New York, Plenum Press, pp. 69–86 (1985).
10. Sarminto, M. et al., Membrane proteins specified by herpes simplex virus III. Role of glycoprotein VP7 (B2) in virion infectivity. *J. Virol.*, 29:1149–58 (1979).
11. Stanberry, L. R. et al., Heterologous Versus Homologous Herpes Simplex Virus Glycoprotein Immunotherapy of Recurrent Genital Herpes. *Pediatr Res.*, 25:191A, Part 2 (1989).
12. Ghiasi, H., Nesburn, A. B. et al., Immunoselection of recombinant baculovirus expressing high levels of biologically active herpes simples virus type 1 glycoprotein D. *Arch. Virol.*, In press. (October 1991).
13. Summers, M. D., Smith, G. E., *A manual of methods for baculovirus vectors and insect cell culture procedures*. Micro Gene Sys., New Haven (1988).
14. Rock, D. L., Nesburn, A. B. et al., Detection of latency related viral RNAs in trigeminal ganglia of rabbits latently infected with herpes simplex virus type 1. *J. Virol.*, 61:3820–26 (1987).
15. Matsuura, Y. et al., Baculovirus expression vectors: the requirements for high level expression of proteins, including glycoproteins. *J. Gen. Virol.*, 68:1233–50 (1987).
16. Inumaru, S. et al., Expression of bluetongue virus group specific antigen VP3 in insect cells by a baculovirus vector: its use for the detection of bluetongue virus antibodies. *J. Gen. Virol.*, 68:1627–35 (1987).
17. Laemmli, U. K., Cleavage of structural proteins during the assembly of the head of bacteriophage T4. *Nature*, 227:680–85 (1970).
18. Towbin, H. T. et al., Electrophoretic transfer of proteins from polyacrylamide gels to nitrocellulose sheets: procedures and some applications. *Proc. Natl. Acad. Sci.*, 76:4350–54 (1979).
19. Jarvis, D. L., Summers, M. D., Glycosylation and secretion of human tissue plasminogen activator in recombinant baculovirus infected insect cells. *Mol. Cell Biol.*, 9:214–23 (1989).
20. Lee, G. T. et al., Location of the structural genes for glycoproteins gD and gE and for other polypeptides in the S component of herpes simplex virus type 1 DNA. *J. Virol.*, 43:41–49 (1982).
21. Mathews, J. T. et al., Synthesis and processing glycoprotein D of herpes simplex virus types 1 and 2 in an in vitro system. *J. Virol.*, 48:521–53 (1983).
22. Takedata, K. et al., Co-expression of the Hepatitis B surface and core antigens using baculovirus multiple expression vectors. *J. Gen. Virol.*, 69:2763–777 (1988).
23. Ghiasi, H. et al., Expression of herpes simplex virus type 1 glycoprotein B in insect cells: Initial analysis of its biochemical and immunological properties. *Virus Research*, 22:25–39(1991).
24. Ghiasi, H., et al., Baculovirus expressed herpes simplex type 1 glycoprotein C protects mice from lethal HSV-1 infection. *Antiviral Research*, 18:291–302(1992).
25. Ghiasi, H., et al., Baculovirus-Expressed Glycoprotein E (gE) of Herpes Simplex Virus Type 1 (HSV-1) Protects Mice against Lethal Intraperitoneal and Lethal Ocular HSV-1 Challenge. *Virology*, 188,469–476 (1992).
26. Ghiasi, H., et al., Baculovirus-Expressed Glycoprotein G of Herpes Simplex Virus Type 1 Partially Protects Vaccinated Mice against Lethal HSV-1 Challenge. *Virology* 190, 233–239 (1992).
27. Ghiasi, H., et al., Cell surface expression of herpes simplex virus type 1 glycoprotein H in recombinant baculovirus infected cells. *Virology*, 185:187–194 (1991).
28. Ghiasi, H., et al., Expression of Herpes Simplex Virus Type 1 Glycoprotein I in Baculovirus: Preliminary Biochemical Characterization and Protection Studies. *J. Virol.*, 66:2505–2509(1992).
29. Morein, B. et al., Iscom, a novel structure for antigenic presentation of membrane proteins from enveloped viruses. *Nature*, 308:457–60 (1984).
30. Goldstein, D. J., Weller, S. K., Factor(s) present in herpes simplex virus type 1 infected cells can compensate for the loss of the large subunit of the viral ribonucleotide reductase: characterization of an ICP6 deletion mutant. *Virology*, 166:41–51 (1988).
31. Shimomura, Y. et al., Shedding by iontophoresis of 6-hydroxdopamine followed by topical epinephrine. *Invest. Ophthalmol.*, 24:1588–90 (1983).
32. Nesburn, A. B. et al., Isolation of herpes simplex virus: Isolation from rabbit trigeminal ganglia between episodes of recurrent ocular infection. *Arch. Ophthalmol.*, 88:412–17 (1972).
33. Nesburn, A. B. et al., Ocular safety and efficacy of an HSV-1 gD vaccine during primary and latent infection. *Invest. Ophthalmol. Vis. Sci.*, 31:77–82 (1990).
34. Ashley, R., Personal communication (1990).
35. Pass, R. F. et al., Identification of Patients With Increased Risk of Infection with Herpes Simplex Virus After Renal Transplantation. *J. Infec. Dis.*, 140(4):487–492 (1979).
36. Borenstein, L. A. et al., Immunization of rabbits with recombinant treponema palladium surface antigen 4D alters the course of experimental syphilis. *J. Immunol.*, 140:2415–21 (1988).

We claim:

1. A method of treating a human host for ocular HSV infections, said method comprising the step of inoculating said host by the ocular route with a therapeutically effective dose of HSV-1 glycoproteins gB and gD in admixture with at least one adjuvant in an effective immunostimulatory amount.

2. The method of claim 1 wherein the ocular route of inoculation is selected from the group consisting of subconjunctival injection, surface drops and a slow-release collagen shield.

3. A method of treating ocular HSV infection in a human host comprising the steps of:

a) inoculating said host by the ocular route with a therapeutically effective dose of HSV-1 glycoproteins gB and gD; and b) inoculating said host by the ocular route with at least one adjuvant.

4. The method of claim 3 wherein said HSV-1 protein is administered in a dose of from about 10–1000 μg per inoculation.

5. The method of claim 3 wherein said adjuvant is inoculated by the ocular route before, simultaneously with or after the ocular inoculation of said HSV-1 glycoproteins.

6. The method of claim 5 wherein said adjuvant is MTP-PE in an effective immunostimulatory amount.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 1204 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
TATAAATACG GATCCTCCGG TATGGGGGGG GCTGCCGCCA GGTTGGGGGC CGTGATTTTG     60
TTTGTCGTCA TAGTGGGCCT CCATGGGGTC CGCAGCAAAT ATGCCTTGGT GGATGCCTCT    120
CTCAAGATGG CCGACCCCAA TCGCTTTCGC GGCAAAGACC TTCCGGTCCT GGACCAGCTG    180
ACCGACCCTC CGGGGGTCCG GCGCGTGTAC CACATCCAGG CGGGCCTACC GGACCCGTTC    240
CAGCCCCCCA GCCTCCCGAT CACGGTTTAC TACGCCGTGT TGGAGCGCGC CTGCCGCAGC    300
GTGCTCCTAA ACGCACCGTC GGAGGCCCCC CAGATTGTCC GCGGGGCCTC CGAAGACGTC    360
CGGAAACAAC CCTACAACCT GACCATCGCT TGGTTTCGGA TGGGAGGCAA CTGTGCTATC    420
CCCATCACGG TCATGGAGTA CACCGAATGC TCCTACAACA AGTCTCTGGG GGCCTGTCCC    480
ATCCGAACGC AGCCCCGCTG GAACTACTAT GACAGCTTCA GCGCCGTCAG CGAGGATAAC    540
CTGGGGTTCC TGATGCACGC CCCCGCGTTT GAGACCGCCG GCACGTACCT GCGGCTCGTG    600
AAGATAAACG ACTGGACGGA GATTACACAG TTTATCCTGG AGCACCGAGC CAAGGGCTCC    660
TGTAAGTACG CCCTCCCGCT GCGCATCCCC CCGTCAGCCT GCCTCTCCCC CCAGGCCTAC    720
CAGCAGGGGG TGACGGTGGA CAGCATCGGG ATGCTGCCCC GCTTCATCCC CGAGAACCAG    780
CGCACCGTCG CCGTATACAG CTTGAAGATC GCCGGGTGGC ACGGGCCCAA GGCCCCATAC    840
ACGAGCACCC TGCTGCCCCC GGAGCTGTCC GAGACCCCCA ACGCCACGCA GCCAGAACTC    900
GCCCCGGAAG ACCCCGAGGA TTCGGCCCTC TTGGAGGACC CCGTGGGGAC GGTGGCGCCG    960
CAAATCCCAC CAAACTGGCA CATACCGTCG ATCCAGGACG CCGCGACGCC TTACCATCCC   1020
CCGGCCACCC CGAACAACAT GGGCCTGATC GCCGGCGCGG TGGGCGGCAG TCTCCTGGCA   1080
GCCCTGGTCA TTTGCGGAAT TGTGTACTGG ATGCGCCGCC ACACTCAAAA AGCCCCAAAG   1140
CGCATACGCC TCCCCCACAT CCGGGAAGAC GACCAGCCGT CCTCGCACCA GCCCTTGTTT   1200
TACT                                                                1204
```